(12) United States Patent
Wasily et al.

(10) Patent No.: US 11,153,076 B2
(45) Date of Patent: Oct. 19, 2021

(54) SECURE COMMUNICATION FOR MEDICAL DEVICES

(71) Applicant: Thirdwayv, Inc., Irvine, CA (US)

(72) Inventors: Nabil Wasily, Foothill Ranch, CA (US); Michael Atef Ayoub, Irvine, CA (US)

(73) Assignee: THIRDWAYV, INC., Irvine, CA (US)

( * ) Notice: Subject to any disclaimer, the term of this patent is extended or adjusted under 35 U.S.C. 154(b) by 253 days.

(21) Appl. No.: 16/133,588

(22) Filed: Sep. 17, 2018

(65) Prior Publication Data

US 2019/0036688 A1    Jan. 31, 2019

Related U.S. Application Data

(63) Continuation-in-part of application No. 16/036,750, filed on Jul. 16, 2018.

(Continued)

(51) Int. Cl.
*H04L 29/06* (2006.01)
*H04L 9/08* (2006.01)
(Continued)

(52) U.S. Cl.
CPC ............ *H04L 9/0825* (2013.01); *G06F 21/35* (2013.01); *G06F 21/44* (2013.01); *G06F 21/606* (2013.01);
(Continued)

(58) Field of Classification Search
CPC ... H04L 9/0825; H04L 9/3213; H04L 9/3231; H04L 9/3247; H04L 9/3268; H04L 63/0823; H04L 63/0428; H04L 63/0861; H04L 63/0876; G06F 21/35; G06F 21/44; G06F 21/606; G06F 21/6245; G06F 21/73; H04W 12/06
See application file for complete search history.

(56) References Cited

U.S. PATENT DOCUMENTS

| 2013/0013095 A1* | 1/2013 | Lu | ................. H04L 9/0877 700/94 |
| 2015/0207626 A1* | 7/2015 | Neftel | ................. G06F 21/35 713/168 |

(Continued)

*Primary Examiner* — Joseph P Hirl
*Assistant Examiner* — Chi D Nguy
(74) *Attorney, Agent, or Firm* — Snell & Wilmer LLP

(57) ABSTRACT

Methods, systems, and apparatus for providing secure communication. The device includes a secure element for generating application key pairs. The device includes a trusted environment that is physically or logically isolated from an untrusted environment. The trusted environment includes one or more processors configured to perform operations of an application. The operations include generating an application key pair. The application key pair includes a secure element private key and a secure element public key. The operations include sending an application authentication request including one or more device identifiers and the secure element public key to a server. The operations include obtaining a digital certificate that includes the secure element public key and the one or more device identifiers. The operations include providing the digital certificate to a second device and establishing a secure communication channel between the device and the second device using the digital certificate.

21 Claims, 10 Drawing Sheets

Related U.S. Application Data

(60) Provisional application No. 62/533,567, filed on Jul. 17, 2017.

(51) Int. Cl.

| | | |
|---|---|---|
| *G16H 80/00* | (2018.01) | |
| *H04L 9/32* | (2006.01) | |
| *G06F 21/60* | (2013.01) | |
| *G06F 21/62* | (2013.01) | |
| *G06F 21/73* | (2013.01) | |
| *G06F 21/35* | (2013.01) | |
| *G06F 21/44* | (2013.01) | |
| *G16H 10/60* | (2018.01) | |
| *G16H 40/67* | (2018.01) | |
| *G16H 40/40* | (2018.01) | |
| *G16H 40/63* | (2018.01) | |
| *H04W 12/06* | (2021.01) | |

(52) U.S. Cl.
CPC .......... *G06F 21/6245* (2013.01); *G06F 21/73* (2013.01); *G16H 80/00* (2018.01); *H04L 9/3213* (2013.01); *H04L 9/3231* (2013.01); *H04L 9/3247* (2013.01); *H04L 9/3268* (2013.01); *H04L 63/0823* (2013.01); *G16H 10/60* (2018.01); *G16H 40/40* (2018.01); *G16H 40/63* (2018.01); *G16H 40/67* (2018.01); *H04L 63/0428* (2013.01); *H04L 63/0861* (2013.01); *H04L 63/0876* (2013.01); *H04L 2209/127* (2013.01); *H04W 12/06* (2013.01)

(56) References Cited

U.S. PATENT DOCUMENTS

| | | | | |
|---|---|---|---|---|
| 2016/0125733 | A1* | 5/2016 | Sallas | G08C 17/02 |
| | | | | 398/106 |
| 2017/0033936 | A1* | 2/2017 | Cidon | H04L 9/3271 |
| 2017/0310647 | A1* | 10/2017 | Hu | G06F 21/33 |
| 2017/0325091 | A1* | 11/2017 | Freeman | A61M 16/0048 |
| 2017/0339144 | A1* | 11/2017 | Han | H04L 49/70 |
| 2018/0123804 | A1* | 5/2018 | Smith | H04W 12/0609 |
| 2018/0288376 | A1* | 10/2018 | Staton | H04N 9/3141 |
| 2019/0250900 | A1* | 8/2019 | Troia | H04W 4/50 |
| 2020/0327230 | A1* | 10/2020 | Bitauld | G06F 21/57 |

* cited by examiner

SECURE COMMUNICATION FOR MEDICAL DEVICES

CROSS-REFERENCE TO RELATED APPLICATIONS

This application is a continuation-in-part of U.S. patent application Ser. No. 16/036,750, titled "SECURE COMMUNICATION FOR MEDICAL DEVICES," filed Jul. 16, 2018, which claims priority to and the benefit of U.S. Provisional Patent Application No. 62/533,567 titled "SECURE COMMUNICATION FOR MEDICAL DEVICES," filed on Jul. 17, 2017, the entire contents of the applications are hereby incorporated by reference herein for all purposes.

BACKGROUND

1. Field

This specification relates to a system, a device and/or a method for secure communication between a personal device, such as a smartphone, a tablet, a laptop or other computer, with another device, such as a medical device.

2. Description of the Related Art

Conventionally, patients, doctors, nurses and other healthcare professionals use a dedicated device to interact with a single medical device, such as a continuous glucose monitor (CGM), an artificial pancreas (AP) system, a pacemaker or an insulin pump. The dedicated device may have a single function or use, such as the control of the CGM or control of the insulin pump. Since the dedicated device has a single function or use, multiple dedicated devices are necessary to address multiple healthcare issues. The use of multiple dedicated devices adds complexity and cost in managing a patient's overall health. Thus, patients, doctors, nurses and other healthcare professionals are transitioning from the use of multiple dedicated devices to the use of smartphones and other multi-use, multi-function personal devices.

These personal devices may run multiple applications that control and interact with the multiple medical devices. Since the personal device runs multiple applications in the same environment, e.g., using the same resources, as the medical applications that operate the medical devices, the medical applications are susceptible to various cybersecurity risks, such as malware, viruses and other vulnerabilities.

Accordingly, there is a need for a system, a method and/or a device that secures the medical applications and communication between the medical applications and medical devices.

SUMMARY

In general, one aspect of the subject matter described in this specification is embodied in a device, a system and/or an apparatus for providing secure communication. The device includes a secure element for generating application key pairs and performing cryptographic operations. The device includes a trusted environment that is physically or logically isolated from an untrusted environment. The trusted environment includes a memory configured to store an application. The trusted environment includes one or more processors configured to perform operations of the application that execute within the trusted environment. The operations include generating an application key pair using the secure element. The application key pair includes a secure element private key and a secure element public key. The operations include sending an application authentication request including one or more device identifiers and the secure element public key to a server. The operations include obtaining, from the server, a digital certificate that includes the secure element public key and the one or more device identifier. The operations include providing the digital certificate to a second device and establishing a secure communication channel between the device and the second device using the digital certificate.

These and other embodiments may optionally include one or more of the following features. The operations may include obtaining the secure element public key. The operations may include storing the secure element public key in the memory and the secure element private key in the secure element. The operations may include digitally signing the application authentication request prior to sending the application authentication request to the server. The digital certificate that is obtained from the server may have been digitally signed by the server.

The one or more device identifiers may include at least one of an application secret, a phone number via a short message service (SMS) code, an e-mail address, a verification code entered into the medical application by a user, remote attestation of the device, remote attestation of the secure element, ownership of the medical device via one or more embedded secrets of the medical device, a user pin code, or one or more biometric identifiers of the user.

The operations may include using the secure element private key to both encrypt and decrypt at least one of application data or secrets for storage in an untrusted environment. The operations may include digitally signing, using the secure element private key stored in the secure element, one or more sensitive payloads. The operations may include communicating the one or more sensitive payloads between the device and the second device. The digital signature may be computed using a secure hash output value and a monotonically increasing counter value. The operations may include establishing, by the application, a shared secret between the device and the second device, the shared secret being based on an exchange of at least one of a device identity, a public key, a digital certificate, a nonce value, or a security proof between the device and the second device.

In another aspect, the subject matter is embodied in a system for providing secure communication. The system includes a medical device. The medical device is configured to provide or administer a medical treatment to a patient. The system includes a server configured to generate a digital certificate in response to authenticating a medical application. The system includes a personal device having a secure element for generating an application key pair and a trusted environment. The trusted environment includes a memory configured to store a medical application. The personal device includes one or more processors configured to perform operations of the medical application that execute within the trusted environment. The operations include generating the application key pair that includes a secure element private key and an secure element public key using the secure element. The operations include forming a application authentication request including one or more device identifiers and the secure element public key to the server. The operations include digitally signing the application authentication request using the secure element private key. The operations include obtaining, from the server, the digital certificate that includes the secure element public key and the one or more device identifiers. The operations include providing the digital certificate to the medical device. The operations include establishing a secure communication channel between the device and the second device using the digital certificate.

In another aspect, the subject matter is embodied in a method for securely communicating between a medical device and an application on a personal device in a secure computing environment. The method includes generating, by the application and using a secure element, a key pair including a secure element private key and a corresponding secure element public key, the application being stored within a trusted environment of the personal device. The method includes storing, by the application and within the secure element, the secure element private key. The method includes sending, by the application and to a server, an application authentication request including the secure element public key and one or more device identifiers. The method includes verifying, by the server, the application authentication request. The method includes generating, by the server, a digital certificate that includes the secure element public key and the one or more device identifiers. The method includes obtaining, by the application, the digital certificate from the server. The method includes establishing, by the application, a secure communication channel between the personal device and the medical device using the digital certificate.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Disclosed herein are systems, devices and methods for securing communication between a personal mobile device and a medical device, such as a continuous glucose monitor (CGM), an artificial pancreas (AP) system, a pacemaker or an insulin pump. The secure communication system has a personal device, such as a smartphone, a tablet, a controller or other handheld or mobile device, which runs a software application that controls, manages and/or otherwise interacts with a medical device. The secure communication system establishes a secure communication channel among the personal device, the medical device and/or the server to ensure that commands, communication and/or other instructions among the devices are secure and protected from viruses, malware, and other security vulnerabilities. This creates a root or a chain of trust that ensures that the commands or other instructions that control the medical device are valid to prevent malicious control of the medical device. Moreover, the use of the personal device instead of a dedicated device to control the medical device allows for the patient, doctor, nurse or other healthcare professional to manage multiple medical devices to control different treatments from a single device. This reduces the overall healthcare cost of the patient, increases convenience and simplifies the control of multiple devices.

Other benefits and advantages include the use of a trusted execution space on the personal mobile device to create a trusted environment. The trusted execution space secures the medical application on the personal mobile device from security vulnerabilities residing on the personal mobile device due to other untrusted applications. The trusted execution space may be a logical and/or a physical separation that protects the operation of the medical application running on the personal mobile device and prevents the risk of exposure to the medical device.

Moreover, the personal device may have an embedded or inserted secure element. The personal device may use the secure element for key pair generation to securely pair the medical application on the personal device with the medical device. The personal device may use the generated key pairs to encrypt/decrypt application data or secrets so that the encrypted application data or secrets may be stored within an untrusted environment or memory. Additionally, the personal device may use the generated key pairs to sign and verify sensitive commands, data and other payloads.

Additionally, since the medical application and implementation is designed to interact with a medical device, the implementation minimizes the amount of resources necessary to secure communication.

Figure 1A:
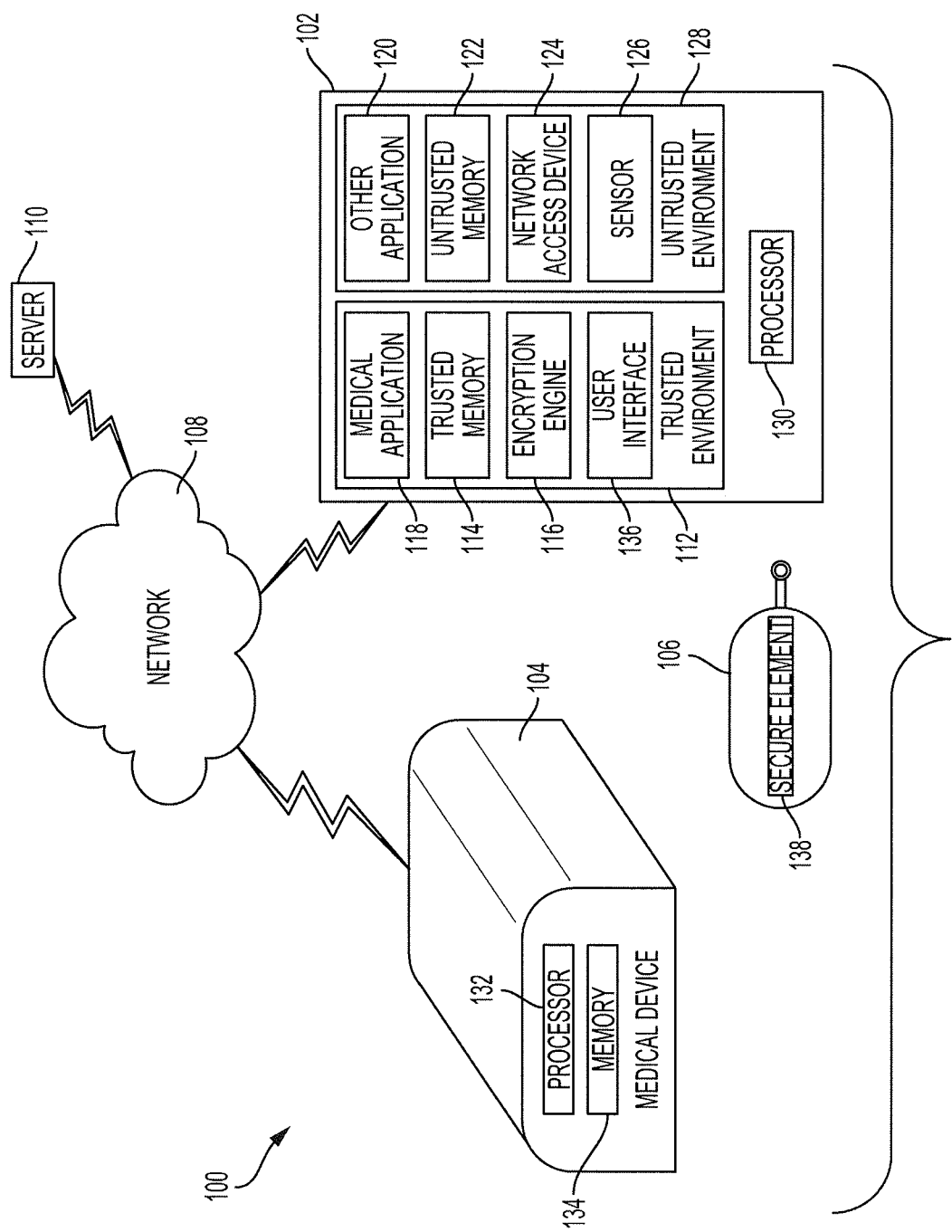
FIG. 1A shows an example block diagram of a secure communication system that establishes secure communication between a personal device and a medical device according to an aspect of the invention.
Figure 1B:
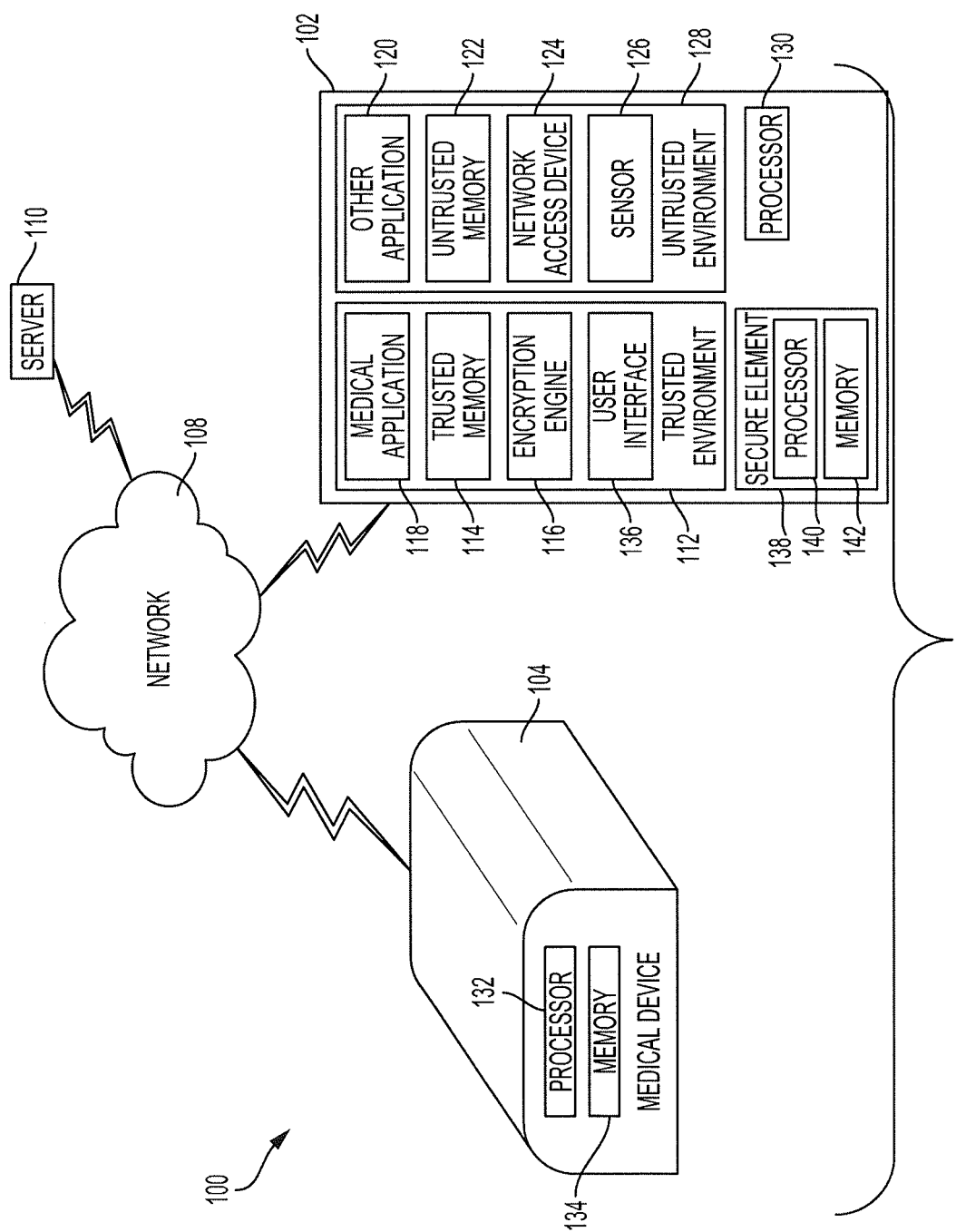
FIG. 1B shows an example block diagram of a secure communication system that includes a personal device having an embedded, inserted or otherwise included secure element according to an aspect of the invention.
Figure 1C:
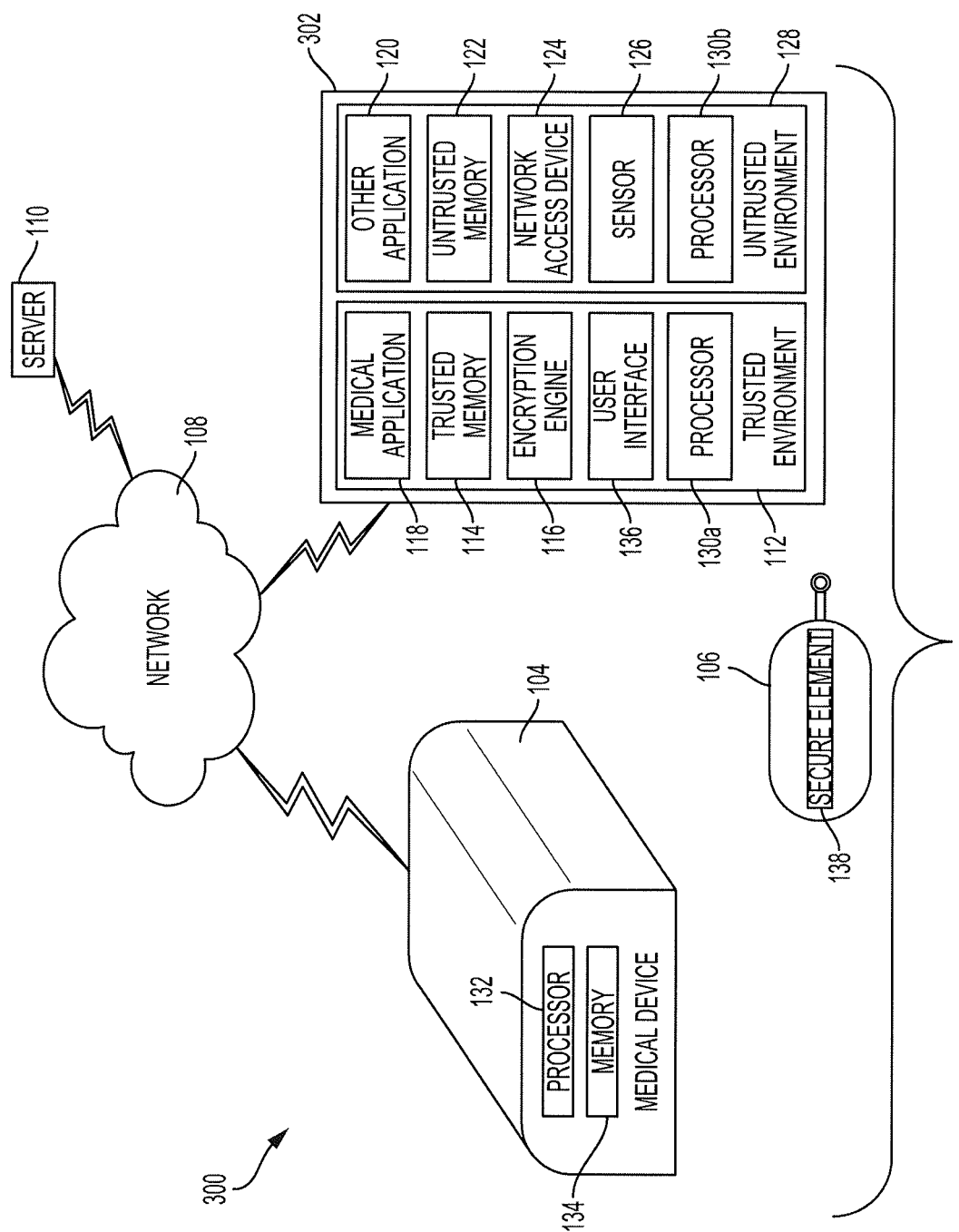
FIG. 1C shows an example block diagram of a secure communication system that includes a personal device having a trusted processor according to an aspect of the invention.

FIGS. 1A-1C show example block diagrams of a secure communication system 100 that establishes secure communication between a personal device 102 and a medical device 104. The secure communication system 100 includes a personal device 102 and a medical device 104. The secure communication system 100 may include a hardware device 106, a network 108 and/or a server 110. The different components, such as the personal device 102, the medical device 104, the server 110 and/or the hardware device 106 may interconnect among each other through the network 108.

The secure communication system 100 includes the personal device 102. The personal device 102 may have an application, such as a medical application 118, which securely controls another device, such as a medical device 104, and other applications 120 loaded on the personal device 102. The medical application 118 controls, manages, communicates and/or otherwise interacts with the medical device 104. The personal device 102 may download the medical application 118 from the server 110. The personal device 102 may use a single medical application 118 to control multiple medical devices and/or have multiple medical applications 118 that each control a corresponding medical device 104.

The personal device 102 has a trusted execution environment ("trusted environment") 112 and an untrusted environment 128. The trusted environment 112 includes a medical application 118, a trusted memory 114, an encryption engine 116 and a user interface 136 within the trusted environment 112. The untrusted environment 128 may include other applications 120, an untrusted memory 122, a network access device 124 and/or a sensor 126. The components within the trusted environment 112 are logically and/or physically isolated from the components within the untrusted environment 128 and may establish a trust zone with a unique identifier. The trusted environment 112 may run a separate and/or a distinct operating system and have distinct resources from the untrusted environment 128. The trusted environment 112 and the untrusted environment 128 may have different processors 130a-b, respectively, within each environment, as shown in FIG. 1C for example, or may share the same processor 130, as shown in FIGS. 1A and 1B, for example.

The trusted environment 112 is a secure environment that is logically and/or physically separated and/or sandboxed from shared resources on the personal device 102. The trusted environment 112 is a dedicated secure environment that has resources, such as a trusted memory 114, processor 130a and/or an encryption engine 116, that are dedicated for the exclusive use of the medical application 118 that resides within the trusted environment 112. The trusted environment 112 sandboxes the medical application 118, the processor 130a, the trusted memory 114 and/or the encryption engine 116 from any of the other applications 120 or other resources on the personal device 102.

The personal device 102 has a medical application 118 within the trusted environment 112. The medical application 118 controls, manages, communicates or otherwise interacts with a medical device 104. For example, the medical application 118 may have or use a user interface 136 that receives input from a user, such as a patient, a doctor, a nurse or other healthcare professional to control or schedule the medical device 104 to dispense or administer medication or the application of treatment. The medical application 118 may communicate with the medical device 104 to dispense or administer the medication or the application of the treatment. In some implementations, the medical application 118 may have a portion of the application residing within the untrusted environment 128 or may interface or connect with other applications and/or components within the untrusted environment 128.

Figure 5:
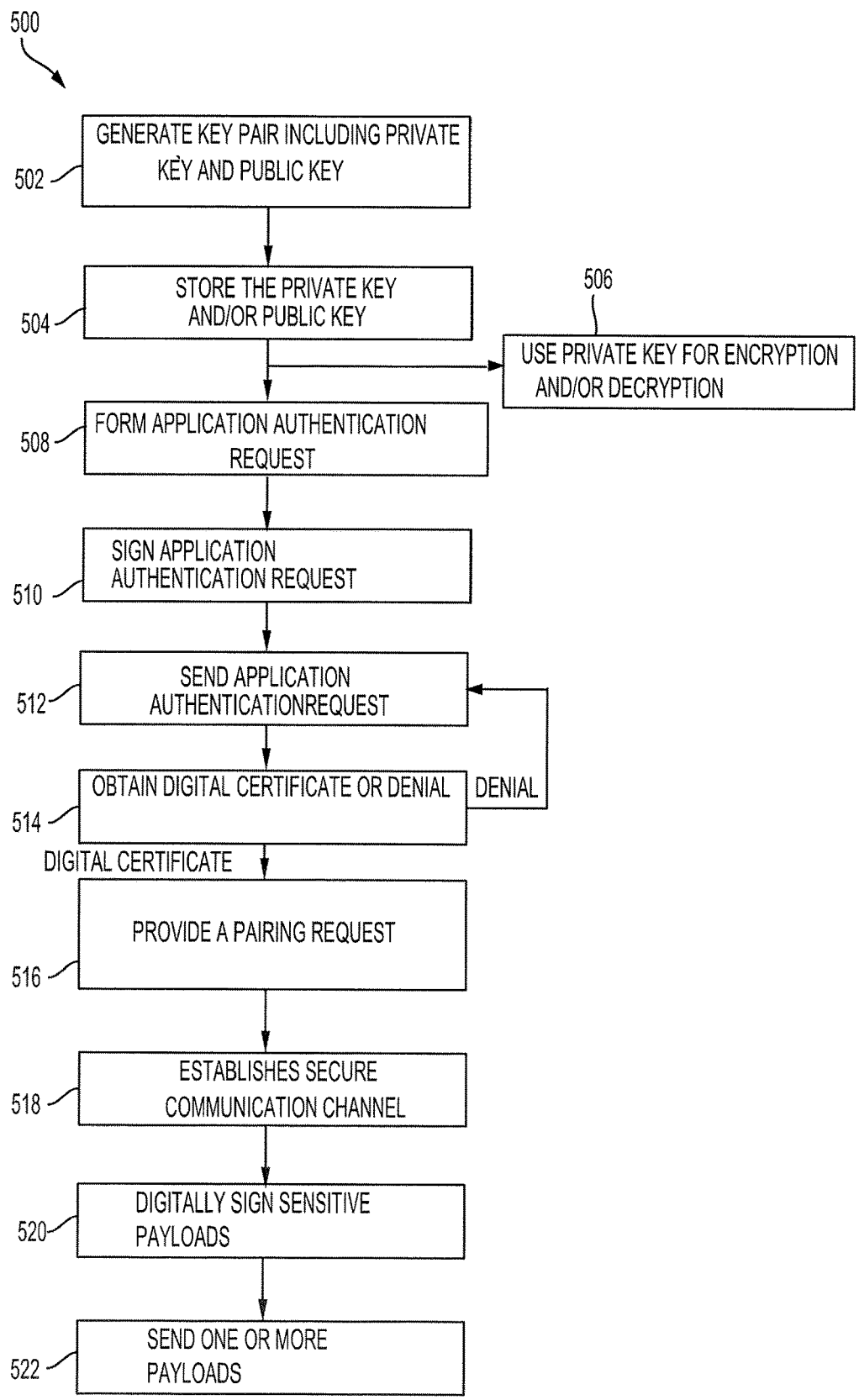
FIG. 5 is a flow diagram of an example process implemented by the personal device to securely pair with the medical device according to an aspect of the invention.

The medical application 118 may be provisioned or downloaded via the server 110 including any certificates that include one or more immutable identifiers. When the medical application 118 is downloaded or provisioned, the medical application 118 may use a secure element 138 to generate the public key and/or the private key, as described in FIG. 5 for example. The medical application 118 may send the public key to the server 110, which may ensure that the medical application 118 sending the public key is authorized to use the public key. The server 110 may validate the medical application 118, validate the integrity of the operating system of the personal device 102 and/or perform other operations to ensure the integrity within the trusted environment 112 and sign the public key once authentication is complete. This ensures that the original operating system has not been modified. FIG. 5 further describes the generation of key pairs and the pairing of the personal device 102 and the medical device 104.

The medical application 118 may be stored in the trusted memory 114. The trusted memory 114 may be within the trusted environment 112. The trusted memory 114 may be a separate physical memory from the untrusted memory 122 or may be the same physical memory as the untrusted memory 122 but logically separated from the untrusted memory 122. The logical and/or the physical separation protects the trusted memory 114 from malware, spyware, viruses and/or other vulnerabilities residing within the untrusted memory 122 and prevents access to the trusted memory 114 by any other application. The trusted memory 114 may store instructions to execute on the processor 130 and may include one or more of a RAM or other volatile or non-volatile memory. The trusted memory 114 may be a non-transitory memory or a data storage device, such as a hard disk drive, a solid-state disk drive, a hybrid disk drive, or other appropriate data storage, and may further store machine-readable instructions, which may be loaded and executed by the processor 130.

The medical application 118 may interact and be connected with an encryption engine 116. The encryption engine 116 may reside within the trusted environment 112. Since the medical application 118 transmits and/or communicates to the medical device 104 using the network access device 124, which resides within the untrusted environment 128, the medical application 118 uses the encryption engine 116 to encrypt any transmissions and/or communications prior to delivering the transmissions and/or communications to the components within the untrusted environment 128. This ensures the integrity and confidentiality of the transmission and/or communication during transit to the medical device 104.

The encryption engine 116 may use a lightweight encryption algorithm, which facilitates decryption by the medical device 104. Since the processor 132 or controller of the medical device 104 does not have significant processing power, the lightweight encryption algorithm allows the medical device to decrypt the transmission and/or communication faster and also requires less processing power for decryption.

The medical application 118 may include, interface and/or interact with the user interface 136. The user interface 136 may be within the trusted environment 112, and thus, be a trusted component. That is, a component within the trusted environment 112, which is segregated, segmented or otherwise sandboxed or isolated from vulnerabilities within the untrusted environment 128. The user interface 136 may include any device capable of receiving user input, such as a button, a dial, a microphone, a graphical user interface or a touch screen, and any device capable of output, e.g., a display, a speaker, or a refreshable braille display. The user interface 136 allows a user to communicate with the medical application 118. For example, the user may be able to provide data to the medical application 118, such as user input, and/or receive feedback from the medical application 118 via the user interface 136. The input may include critical input, such as control and/or administration of the treatment and/or medication. The user interface 136 may display notifications and/or confirmations, e.g., to activate or deactivate the medical device 104. The user interface 136 may display a secret phase/image to protect the user from phishing attacks.

The personal device 102 includes a processor 130. The processor 130 may be a single processor or multiple processors 130*a-b*. The processor 130 may receive data from one or more components and control the operations of the one or more components based on the received or determined data. For example, the processor 130 may run the medical application 118 to control a medical device 104 by transmitting commands and/or instructions from the medical application 118 to the medical device 104 through untrusted components, such as the network access device 124. The processor 130 may reside within the trusted environment 112, the untrusted environment 128 or both. For example, portions of the processor 130 may be within the trusted environment 112 and logical and/or physically segregated from other portions of the processor 130 within the untrusted environment 128. In another example, the personal device 102 has multiple processors 130*a-b*. The processor 130*a* may be a trusted processor that may reside within the trusted environment 112. The processor 130*b* may be an untrusted processor that may reside within the untrusted environment 128.

The personal device 102 may have an untrusted environment 128. The untrusted environment 128 may use shared resources for all the other applications 120 and may be segregated, logically, physical or both, from the trusted environment 112. Since the untrusted environment 128 shares resources among all the other applications 120, the shared resources, the other applications 120 and any other communications and/or instructions that traverse the untrusted environment may be susceptible to vulnerabilities.

The other applications 120 may be within the untrusted environment 128. The other applications 120 may include a web browser, a mobile game, a social networking application or other mobile user application(s) designed to operate on the personal device 102. These other applications 120 may be downloadable from an online store but may be unrelated to the control and/or operations of the medical device 104 and may have not undergone security testing and verification. Thus, these other applications 120 may be susceptible to application level vulnerabilities, network level vulnerabilities, operating system level vulnerabilities or other vulnerabilities. The other applications 120 reside within the untrusted memory 122.

The untrusted memory 122 is a separate memory from the trusted memory 114 and may reside within the untrusted environment 128. The untrusted memory 122 may be logically and/or physically separated from the trusted memory 114 to maintain the security of the trusted memory 114. The untrusted memory 122 may store instructions to execute on the processor 130 and may include one or more of a RAM or other volatile or non-volatile memory. The untrusted memory 122 may be a non-transitory memory or a data storage device, such as a hard disk drive, a solid-state disk drive, a hybrid disk drive, or other appropriate data storage, and may further store machine-readable instructions, which may be loaded and executed by the processor 130.

The personal device 102 uses the network access device 124 to establish a connection with the medical device 104. The medical application 118 may send a command and/or an instruction using the network access device 124 to the medical device 104 through the network 108. Since the network access device 124 resides within the untrusted environment 128, the medical application 118 uses the encryption engine 116 to encrypt, sign or otherwise secure the command and/or instruction to ensure that the message is not modified or otherwise accessed prior to using the network access device 124 to send the message.

The network access device 124 may include a communication port or channel, such as one or more of a Wi-Fi unit, a Bluetooth® unit, a radio frequency identification (RFID) tag or reader, or a cellular network unit for accessing a cellular network (such as 3G or 4G). The network access device 124 may transmit data to and receive data from devices and systems not directly connected to the personal device 102. For example, the medical application 118 may communicate with the medical device 104 and/or the server 110 through the network 108.

The personal device 102 may have one or more sensors 126. The one or more sensors 126 may be within the trusted environment 112 and/or the untrusted environment 128. The one or more sensors 126 may include a proximity sensor. The proximity sensor may detect or measure a distance between the personal device 102 and the medical device 104. If the distance is less than a threshold distance, the proximity sensor may indicate to the processor 130 that the personal device 102 is within proximity to or within a threshold distance of the medical device 104. The processor 130 may allow for the authentication process between the personal device 102 and the medical device 104 to begin in order to establish a connection between the personal device 102 and the medical device 104.

The network 108, such as Bluetooth Low Energy (BLE) network, a local area network (LAN), a wide area network (WAN), a cellular network, the Internet, or combination thereof, connects the personal device 102 to the one or more medical devices 104 and/or the server 110. The server 110 may store a cloud authentication token, a database on immutable identifiers and/or certificates and/or other verification database to verify the validity and/or authenticity of one or more authentication factors. The server 110 may be a trusted application management (TAM) server, for example. When the personal device 102 connects with the medical device 104, the personal device 102 and the medical device 104 may not rely on the standard authentication methods, but instead, the personal device 102 and the medical device 104 may rely on an added upper layer authentication that runs on top of the network communication.

The secure communication system 100 may include a hardware device 106. The hardware device 106 may be a smartwatch, a fitness tracker, the medical device 104 or another device with an embedded hardware secure element ("secure element") 136, as shown in FIG. 1A for example. A secure element 138 has anti-tamper and anti-cloning features. The secure element 138 may provide key generation, key storage and/or other cryptographic functions. In some implementations, the secure element 138 is included in, embedded within or inserted into the personal device 102, as shown in FIG. 1B for example. The secure element 138 may be a secure element chip, which may be an integrated circuit and/or memory that securely stores certificates, keys or other authentication or identification information data. The secure element 138 may have a secure element processor 140, a secure element memory 142 and/or a secure element non-volatile memory, such as a flash. The secure element processor 140 and/or the secure element memory 142 may be similar to any other processor or memory, described herein, but may have less processing power or less storage, respectively. The secure element 138 may be inserted into the personal device 102, much like a subscriber identification module (SIM) card or a secure digital (SD) card, or may be embedded or included within the personal device 102 but physically and/or logically separated and isolated from other resources of the personal device 102. The medical application 118 uses the secure element 138 to generate private/public key pairs and store the private key. The medical application 118 and/or secure element 138 use the private key for the encryption/decryption of sensitive payloads and for the signing of sensitive messages and commands.

The hardware device 106 may interact with the medical device 104 to provide to the medical device 104 one or more authentication factors, such as a hardware token, to authenticate the personal device 102. The hardware device 106 may be provided to the user and may need to be in proximity to the medical device 104 to provide the one or more authentication factors to the medical device 104. The hardware device 106 may transmit a hardware authentication token to the medical device 104 when the hardware device 106 is in proximity to the medical device 104. The hardware device 106 may have a hardware secure element that stores one or more certificates, such as the certificate for the medical application 118 of the personal device 102, and/or passwords, which is communicated, e.g., as a hardware authentication token, to the medical device 104 as an authentication factor. The hardware device 106 may have a user interface that allows the password to be entered.

The secure communication system 100 includes a medical device 104. The medical device 104 may be a as a continuous glucose monitor (CGM), an artificial pancreas (AP) system, a pacemaker or an insulin pump or other medical device that administers treatment, dispenses medication or performs other medical functions or procedures on a patient.

The medical device 104 may include a processor 132 and/or a memory 134. The processor 132 may be a single processor or multiple processors. The processor 130 may receive data from one or more components and control the operation of the one or more components based on the received or determined data. For example, the processor 132 may communicate with the medical application 118 and control the medical device 104. The processor 132 may transmit a response to the medical application 118 and verify one or more authentication factors and/or signatures sent by the medical application 118. The processor 132 may receive instructions from the medical application 118 and control the medical device 104. The processor 132 may perform decryption of the transmission and/or communication. The processor 132 may use a server secret to authenticate, encrypt and/or decrypt secure over-the-air firmware updates. The processor 132 verifies a firmware signature on the firmware to securely boot the firmware on the medical device 104.

The memory 134 may be a non-transitory memory or a data storage device, such as a hard disk drive, a solid-state disk drive, a hybrid disk drive, or other appropriate data storage, and may further store machine-readable instructions, which may be loaded and executed by the processor 132. The memory 134 may store a firmware update to the medical device 104, which is used to securely boot the medical device 104.

Figure 2:
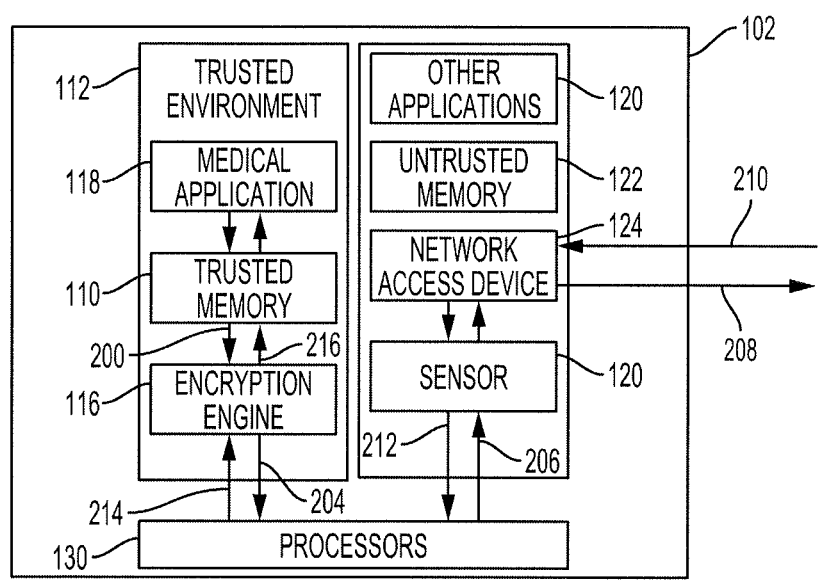
FIG. 2 shows an example personal device of the secure communication system and the secure communication channels within the personal device according to an aspect of the invention.

FIG. 2 shows an example personal device 102 and the secure communication within the personal device 102. The medical application 118 resides within the trusted environment 112, which is a self-contained environment. The trusted environment 112 sandboxes or isolates the components, such as the medical application 118, the trusted memory 114 and the encryption engine 116, from other resources, such as other applications 120. This protects the medical application 118 from malware, spyware, viruses or other vulnerabilities directed at and/or within other resources.

The medical application 118 uses a trusted memory 114 that is separated from and is not shared with the other resources. This dedicated memory ensures that the medical application 118 resides within a clean environment, i.e., an environment free from malware, spyware, viruses, root kits or other vulnerabilities. Moreover, the medical application 118 may send any and all communications, commands and/or instructions along path 200 to the encryption engine 116 prior to transmission and/or communication to the medical device 104. The path 200 resides entirely within the trusted environment 112, and so, the transmission and/or communication may be in plain text and still maintain integrity without concern for any tampering or modification. The encryption engine 116, which resides within the trusted environment 112, encrypts the transmission and/or communication prior to sending the communication to the network access device 124 for transmission to the medical device 104. The encryption of the transmission and/or communication, while within the trusted environment, ensures integrity and confidentiality of the transmission and/or communication.

The encryption engine 116 provides the encrypted transmission and/or communication through the processor 130 along the paths 204, 206 to the network access device 124 to be transmitted out along the path 208 to the medical device 104. While the transmission and/or communication transmits through the untrusted environment 128 and the network 108, which are unprotected and susceptible to malicious attacks, the encryption protects the confidentiality and integrity of the transmission and/or communication. This prevents unauthorized modification, tampering and/or access to the transmission and/or communication.

The network access device 124 may receive an encrypted transmission and/or communication from the medical device 104 along the path 210 and pass the encrypted transmission and/or communication through the processor 130 to the encryption engine 116 via the paths 212, 214. The encryption engine 116 decrypts the transmission and/or communication prior to sending the transmission and/or communication to the medical application 118 along the path 216.

Figure 3:
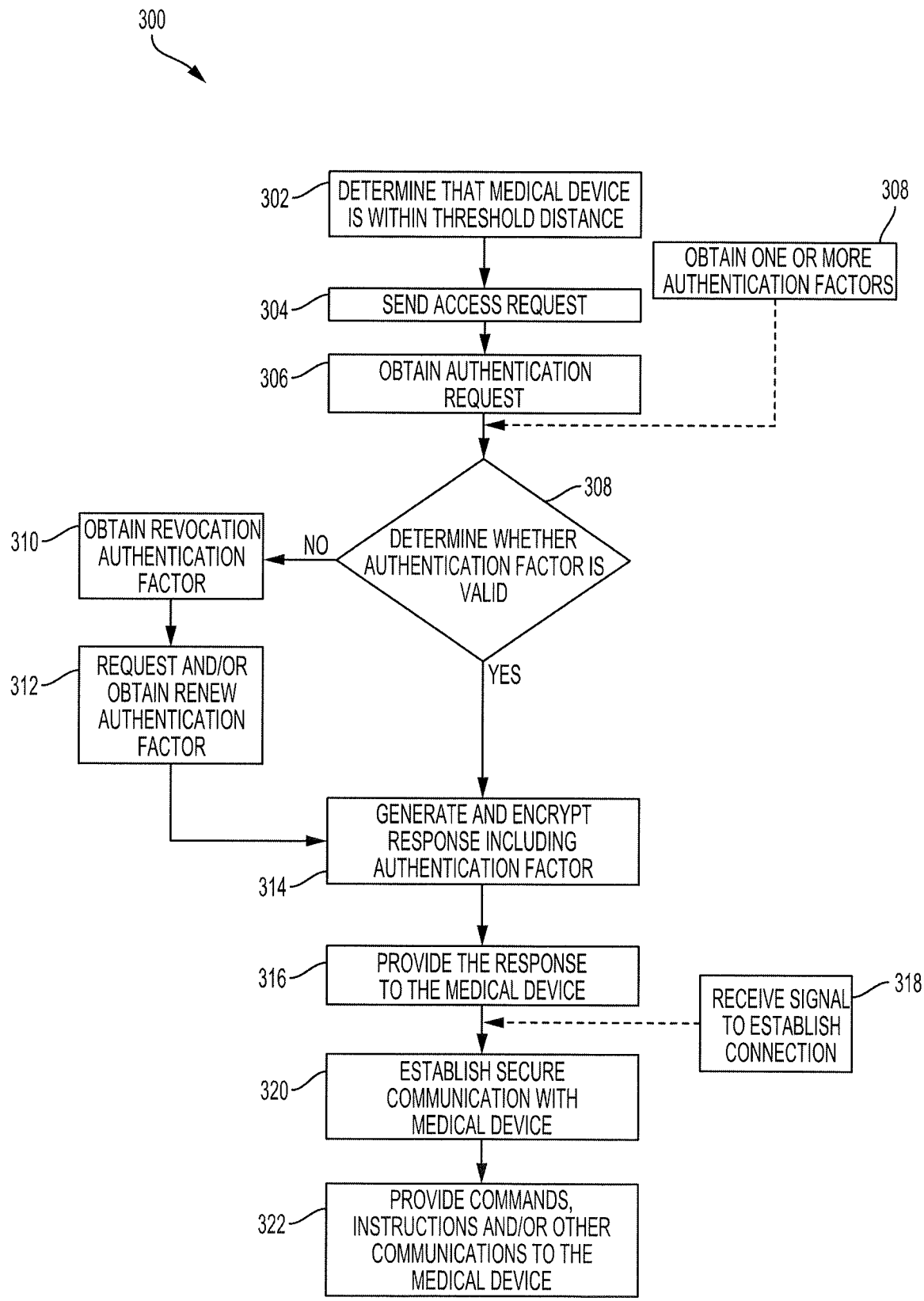
FIG. 3 is a flow diagram of an example process implemented by the personal device to securely connect with the medical device according to an aspect of the invention.

FIG. 3 is a flow diagram of a process 300 implemented on the personal device 102 to securely connect with the medical device 104. The one or more computers or data processing apparatuses, for example, the processor 130 or trusted processor 130a in conjunction with other components, such as the medical application 118, of the secure communication system 100 of FIG. 1, appropriately programmed, may establish a secure connection between the personal device 102 and the medical device 104.

The personal device 102 may determine that the personal device 102 is within proximity or within a threshold distance of the medical device 104 (302). The personal device 102 may use a sensor 126, such as a proximity sensor, to measure a distance to the medical device 104 and determine that the distance is less than the threshold distance. In some implementations, the sensor 126 may detect whether the medical device 104 is within the threshold distance. The proximity sensor may transmit, for example, an electromagnetic field or an electromagnetic beam and look for changes in the field or a return signal. In some implementations, the network access device 124 may passively discover, scan or search for the medical device 104 and attempt to pair with the medical device 104 when the medical is discovered.

The personal device 102 may send an access request to the medical device 104 (304). The access request includes a request to establish a connection with the medical device 104. The access request may include a command and/or other operation or instruction that controls a function of the medical device 104. For example, the command may control the administration of a treatment or medication, such as dispensing insulin. The access request may identify the medical application 118 of the personal device 102 as a device manager of the medical device 104 and/or the device manager of multiple different medical devices.

The access request may include one or more immutable identifiers of the personal device 102. The one or more immutable identifiers of the personal device 102 may be an International Mobile Equipment Identity (IMEI) number, a phone number, a Bluetooth Low Energy (BLE) Media Access Control (MAC) address. The one or more immutable identifiers are specific identifiers of the personal device 102 that are immutable and/or unchangeable.

The personal device 102 may obtain an authentication request from the medical device 104 (306). The network access device 124 may receive the authentication request from the medical device 104. The encryption engine 116 may decrypt the authentication request and the medical application 118 may present, render or otherwise display the authentication request to the user of the personal device 102.

The authentication request may include a request for one or more authentication factors. The one or more authentication factors may be provided to the medical device 104 to verify, authenticate or authorize the personal device 102 with the medical device 104. After verification, authentication or authorization of the personal device 102 with the medical device 104, the personal device 102 and/or the medical device 104 may establish a secure connection.

The personal device 102 may obtain one or more authentication factors (307). The one or more authentication factors may include a certificate, a password, a hardware authentication token and/or a cloud authentication token. The password may be provisioned at manufacturing, fabrication, packaging or distribution of the medical device 104 and may contain any number of alphanumeric characters of any length, such as a password length of 5 alphanumeric characters or 20 bits. The password may be written within a packaging or within a manual of the medical device 104, such that a user of the medical device 104 and/or the personal device 102 has access to the password. For example, the medical application 118 may present a user interface 136 on the personal device 102 and receive user input through the user interface 136 to obtain the password that was provisioned with the medical device 104 and/or provisioned with the medical application 118, when the medical application 118 was loaded on the personal device 102.

The password may be a zero-knowledge password proof (ZKPP). A zero-knowledge password proof is where one party, such as a user or the medical application 118 on the personal device 102, proves to another party, such as the medical device 104, that it knows a password or key without revealing anything other than the fact that it knows the password to the other party. In some implementations, the password may be lightweight, which minimizes the amount of resources needed by the medical device 104 to verify the password. The lightweight password may be injected or used with an Elliptic Curve Diffie-Hellman pairing algorithm, for example.

The certificate may be a device certificate. The medical application 118 of the personal device 102 may obtain the device certificate from a server 110 through the network 108. The server 110 may perform the functions of a certificate and/or signature authority and sign the device certificate using a private key. A certificate and/or signature authority stores, issues and signs the digital certificates. The server 110 may revoke and/or renew the device certificates of the personal device 102. Upon download of the medical application 118, the medical application 118 may request and/or obtain the device certificate from the server 110 and provision the device certificate during download of the medical application 118.

The device certificate may have one or more immutable identifiers that are bonded to the device certificate. The one or more immutable identifiers may include an International Mobile Equipment Identity (IMEI) number, a phone number, a Bluetooth Low Energy (BLE) Media Access Control (MAC) address, a TrustZone Identifier (ID) or other identifier that is bound and associated with the device certificate. The one or more immutable identifiers may be used by the medical device 104 to verify, authenticate and/or authorize the device certificate and the personal device 102. Other types of authentication factors may include a cloud authentication token and/or a hardware authentication token.

The personal device 102 may obtain the hardware authentication token, such as a password, personal identification number (PIN) or other secret, which originates on the hardware device 106. For example, the hardware device 106 may display a password or PIN, and the personal device 102 may request and receive user input of the password or PIN displayed on the hardware device 106. In another example, the hardware device 106 may be paired with the medical application 118 of the personal device 102 using a certificate.

In some implementations, the personal device 102 may obtain multiple authentication factors, such as a password and a certificate, based on the authentication request to authenticate the personal device 102 with the medical device 104. One or more other devices, such as the hardware device 106, may have one of the one or more authentication factors, such as the hardware authentication token, and provide the one or more authentication factors to the personal device 102 to assist to establish a connection between the personal device 102 and the medical device 104. The personal device 102 may obtain a message and/or a cloud authentication token from the medical device 104 that indicates to the server 110 to verify the personal device 102. The personal device 102 transmits this message and/or cloud authentication token to the server 110 for signature. The server 110 returns the signed message to the medical device 104 to be verified. The message may have been encrypted with the symmetric key shared only between the server 110 and the medical device 104 so no unauthorized application or device may modify the message during transit. The symmetric key may be shared between the medical device 104 and the server 110 during manufacturing, distribution and/or provisioning of the medical device 104.

The personal device 102 may determine whether the one or more authentication factors are valid (308). The personal device 102 may use the server 110 to determine whether the one or more authentication factors are valid. For example, the personal device 102 may analyze the certificate and determine an expiration date of the certificate. In some implementations, the personal device 102 may send the certificate to a server 110, which determines the expiration date of the certificate and a current date and compares the current date with the expiration date to determine the validity of the certificate.

If the authentication factor is not valid, the personal device 102 may obtain a revocation of the authentication factor from the server 110 (310). For example, if the current date of the certificate is past the expiration date, the server 110 may revoke the certificate and send the revocation to the personal device 102, which obtains the revocation. The medical application 118 may delete or otherwise render inoperable the establishment of a communication channel until a new certificate is obtained.

In response to the authentication factor, such as the certificate, being revoked, the personal device 102 may request and/or obtain a renewal of the authentication factor (312). For example, the personal device 102 may request a renewal of the certificate and the server 110 may issue a new certificate and send the new certificate to the personal device 102. The personal device 102 uses the new certificate to replace or renew the expired certificate and store the new certificate in the trusted memory 114.

After the authentication factors has been renewed or if the authentication factor is valid, the personal device 102 may generate a response to the medical device 104 and encrypt the response to the medical device 104 (314). The response may include the one or more authentication factors to send to the medical device 104 to establish the secure connection. The response may include additional information, such as the communication protocol, to establish the connection between the personal device 102 and the medical device 104 using an Elliptic Curve Diffie-Hellman algorithm, for example. The personal device 102 may use the encryption engine 116 to encrypt the response to the medical device 104. The encryption protects the response from unauthorized modification and/or access, which preserves both the confidentiality and integrity of the response when the response is provided to the untrusted components within the untrusted environment 128 for transmission.

The personal device 102 provides or sends the response to the medical device 104 (316). The personal device 102 may use the network access device 124 to send the response to the medical device 104 across a wired or wireless connection. The response includes the one or more authentication factors requested by the medical device 104 for authentication and establishment of the communication channel. Once the one or more authentication factors are validated or verified by the medical device 104, the personal device 102 may receive a signal to establish a connection (318), and in response, establish the secure communication with the medical device 104 (320). The secure communication allows the medical application 118 to communicate with the medical device 104 and provide a secure channel between the medical application 118 and the medical device 104 that protects the integrity and confidentiality of communication within the secure channel.

The personal device 102 may provide commands, instructions and/or other communications within the established communication to control the medical device 104 (322). The commands, instructions and/or other communications may cause the medical device 104 to administer a treatment or medication to a patient, for example.

Figure 4:
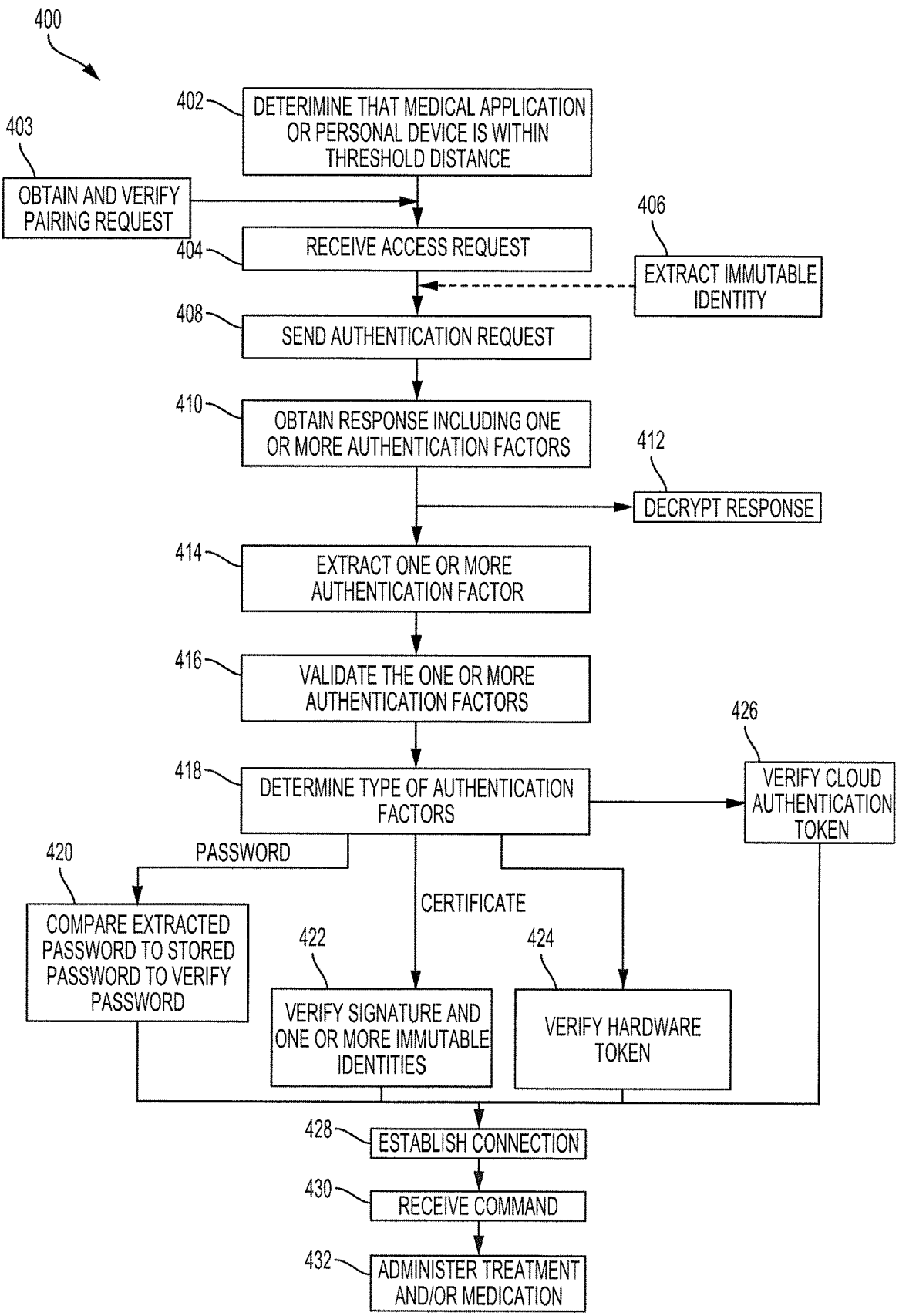
FIG. 4 is a flow diagram of an example process implemented by the medical device to securely connect with the personal device according to an aspect of the invention.

FIG. 4 is a flow diagram of a process 400 implemented on the medical device 104 to securely connect with the personal device 102. The one or more computers or data processing apparatuses, for example, the processor 132 in conjunction with other components, such as the memory 134, of the secure communication system 100 of FIG. 1, appropriately programmed, may establish a secure connection between the personal device 102 and the medical device 104.

The medical device 104 may determine that the personal device 102 is within a threshold distance (402). The medical device 104 may passively discover, scan or search for the personal device 102 to attempt to pair with the personal device 102 when discovered. In some implementations, the medical device 104 is in a passive state awaiting an access request from the medical application 118 on the medical device 104.

The medical device 104 may obtain and verify a pairing request from the personal device 102 to pair the two devices (403). The pairing request may include a digital certificate. The medical device 104 may verify the digital certificate prior to pairing with the medical application 118 of the personal device 102. The medical device 104 may have been provision with the server public key and extract the secure element public key from the digital certificate included with the pairing request. For example, the medical device 104 may use the server 110 public key to verify a digital signature on the digital certificate and a secure element public key to verify other payloads. The medical device 104 may extract one or more device identifiers and provide the one or more device identifiers to the server 110 for verification prior to pairing with the personal device 102. Once verified, the medical device 104 pairs with the personal device 102.

The medical device 104 may obtain an access request from the personal device 102 (404). When the medical device 104 obtains the access request from the personal device 102, the medical device 104 may extract from the access request or the protocol used to transmit the access request the one or more immutable identifiers of the personal device 102, such as the IMEI number, the phone number, the BLE MAC address, a TrustZone Identifier (ID) or other identifier (406). The medical device 104 may parse and/or analyze the protocol used to communicate the access request to determine the one or more immutable identifiers of the personal device 102 and use the one or more immutable identifiers for verification using the server 110, for example.

In response to obtaining the access request, the medical device 104 may provide or send an authentication request (408). The authentication request may include a request for a single authentication factor and/or a request for multiple authentication factors. The multiple authentication factors may be of different types and requested from the personal device 102, the hardware device 106, the server 110 and/or combinations thereof. That is, the authentication request may request any number of different authentication factors, such as a password, a certificate, a hardware authentication token and/or a cloud authentication token.

For example, the medical device 104 may request the password and/or the certificate from the medical application 118 of the personal device 102. In another example, the medical device 104 may request the hardware authentication token from a separate hardware device 106 in addition or in combination with the request for the password and/or the certificate from the medical application 118 of the personal device 102. The separate hardware device 106 may be provided to the user via a different distribution channel, such as through the mail, to ensure that the original user that received the hardware device 106 is the same user as the user of the personal device 102. In another example, the medical device 104 may send a message with a cloud authentication token to the server 110 via the personal device 102. The medical device 104 and the server 110 may share a symmetric key that is used to encrypt the message so that the personal device 102 or other unauthorized device may not be able to manipulate or modify the message. The message may indicate that the personal device 102 should be an authenticated device.

The medical device 104 may obtain one or more responses that include the one or more authentication factors (410). The medical device 104 may obtain the one or more responses from different devices, such as the personal device 102, the server 110, the hardware device 106 or a combination thereof, based on the type of one or more authentication factors requested. For example, if the medical device 104 sent an authentication request that requested a password and a hardware authentication token, the medical device 104 may anticipate to receive two responses, one response from the medical application 118 on the personal device 102 and another response from the hardware device 106. In another example, the medical device 104 may receive a response from the server 110 that is signed via the personal device 102. The response may indicate that the personal device 102 is authenticated and that the medical device 104 may establish a connection with the personal device 102.

The medical device 104 may decrypt the one or more responses if the one or more responses are encrypted (412). The medical device 104 may use an Elliptic Curve Diffie-Hellman pairing algorithm that is lightweight to minimize the use of resources on the medical device 104 to decrypt the one or more responses.

The medical device 104 may extract the one or more authentication factors from the one or more responses (414). The medical device 104 may determine the type of authentication factor extracted from the one or more responses and authenticate the one or more authentication factors based on the type of authentication factor (416). For example, the medical device 104 may determine whether the authentication factor is a password, a hardware authentication token, a certificate and/or a cloud authentication token.

If the one or more authentication factors include a password, the medical device 104 may compare the extracted password from the one or more responses to a stored password that was provisioned during manufacturing, fabrication and/or distribution (418). If the extracted password and the stored password match, the medical device 104 validates the particular authentication factor of the one or more authentication factors. The medical device 104 may mutually authenticate the extracted password and the stored password to pair the medical device 104 with the medical application 118 on the personal device 102. The medical device 104 and the personal device 102 may use a cryptographic password authenticated pairing and/or key derivation/agreement, e.g., Secure Remote Password (SRP) or Password Authenticated Connection Establishment (PACE) algorithms, to pair the two devices. In some implementations, the medical device 104 uses a lightweight password, which may be injected or used with an Elliptic Curve Diffie-Hellman pairing algorithm, for example, as the cryptographic password authenticated pairing and/or key derivation/agreement.

If the one or more authentication factors include a certificate, the medical device 104 may verify a signature on the certificate and/or verify one or more immutable identifiers to determine the validity of the certificate (420). The medical device 104 may validate the signature and verify the issuer of the certificate to establish a chain of trust with the personal device 102. The medical device 104 may extract one or more immutable identifiers from the certificate and compare the one or more immutable identifiers from the certificate with the one or more immutable identifiers of the personal device 102 and verify that the immutable identifiers match. For example, the medical device 104 may compare and verify that the phone number of the personal device 102 matches a phone number assigned to the certificate. In another example, the medical device 104 may compare and verify that the BLE MAC address, the IMEI number or the TrustZone Identifier (ID) of the personal device 102 matches the BLE MAC address, the IMEI number, and/or the TrustZone Identifier (ID) assigned to the certificate, respectively. In some implementations, the medical device 104 may verify all or any number of the immutable identifiers. If the chain of trust is established and the immutable identifiers match, the medical device 104 validates the certificate and personal device 102.

In some implementations, the medical device 104 may use or query the server 110 to verify the one or more immutable identifiers, such as the TrustZone ID, and/or validate the certificate. The medical device 104 may send the immutable identifier to the server 110, which verifies the immutable identifier, or provides other information such as a phone number, an IMEI number or other identifier to the medical device 104 with which the medical device 104 may use to compare with the one or more immutable identifiers of the personal device 102.

In some implementations, the medical device 104 may provide a medical device certificate of the medical device 104 to the personal device 102. The medical device certificate may be provisioned during manufacturing and stored in flash or a hardware secure element.

If the one or more authentication factors include a hardware authentication token, the medical device 104 may receive the hardware authentication token from a hardware device 106 that is in proximity to the medical device 104 and verify that the hardware authentication token matches a pre-programmed or provisioned token (422). The hardware device 106 may pair the hardware authentication token with the medical application 118 and be used as one of the one or more authentication factors to authenticate the establishment of the secure communication channel between the personal device 102 and the medical device 104. The hardware device 106 may be pre-paired with the medical application 118 of the personal device 102 and may have a hardware authentication token that may include a certificate or require a personal identification number (PIN) or password. The medical device 104 may require that the hardware device 106 with the hardware authentication token be present along with the medical application 118 of the personal device 102 in order to authenticate the medical application 118 of the personal device 102. The medical device 104 may receive the hardware authentication token including the certificate, a PIN, and/or a password from the hardware device 106 along with any other authentication factors from the personal device 102 to authenticate the medical application 118 of the personal device 102. In some implementations, the medical device 104 may use the hardware authentication token to confirm one or more critical commands, such as the administration of a treatment or a medication.

The medical device 104 may receive the hardware authentication token from the hardware device 106 over an "alternate radio," such as Sub-GHz radio or ANT+. The use of an "alternate radio" protects the communication between the hardware device 106 and the medical device 104 to prevent scalable attacks.

If the one or more authentication factors include a cloud authentication token, the medical device 104 may verify the signature on the cloud authentication token to ensure that the message received with the cloud authentication token is valid and from the server 110 (424). The message may indicate that the personal device 102 is authenticated and may establish a communication channel with the medical device 104.

In some implementations, the one or more authentication factors include multiple authentication factors. If the medical device 104 requires multiple authentication factors to establish a secure connection, the medical device 104 must validate the multiple authentication factors prior to establishing the secure connection. That is, all the required authentication factors must be verified. For example, if the medical device 104 requires a valid password and a valid certificate, both the password and the certificate must be validated prior to establishing the secure connection with the personal device 102.

Once the medical device 104 authenticates the one or more authentication factors, the medical device establishes a connection with the medical application 118 of the personal device 102 (426). The medical device 104 may receive a command, an instruction or other communication from the medical application 118 that controls the medical device 104, which may require additional verification of another authentication factor (428). The medical device 104 administers treatment or medication based on the command, the instruction or other communication from the medical application 118 (430).

FIG. 5 is a flow diagram of a process 500 implemented on the personal device 102 to obtain the digital certificate from the server 110 and pair with the medical device 104 using the digital certificate. The one or more computers or data processing apparatuses, for example, the processor 130, secure element processor 140 or the trusted processor 130a in conjunction with other components, such as the medical application 118 and/or the secure element 138, appropriately programmed, may pair the personal device 102 and the medical device 104. The secure element 138 may perform the cryptographic and/or key generation functions or the medical application 118 may use the secure element 138 to perform the cryptographic and/or key generation functions, e.g., by using the secure element 138 to perform the function.

When the personal device 102 has a secure element 138, the personal device 102 may use the secure element 138 to generate a key pair including a secure element public key and a secure element private key (502). The medical application 118 uses the secure element 138 to generate the key pair when the medical application 118 is downloaded. For example, the secure element 138 may generate the secure element public key and the secure element private key. The secure element 138 may provide and the medical application 118 may obtain the secure element public key from the secure element 138. In some implementations, the personal device 102 may generate the key pair in response to a user-inputted command.

The personal device 102 using the secure element 138 may generate a primary key pair, including a primary private key and a primary public key, and a secondary key pair, including a secondary private key and a secondary public key. The primary private key may require user identity authentication before the primary private key is used. For example, when the medical application 118 may use the primary private key to perform data encryption.

The personal device 102 may store the secure element private key and/or the secure element public key (504). The secure element 138 may store the secure element private key in the secure element memory 142 and the secure element public key in the trusted memory 114. The medical application 118 may use the secure element private key to both encrypt and decrypt application data, data stored in the untrusted memory 122, or data stored on a server 110 (506). This allows the medical application 118 to securely store data and/or secrets in an encrypted form in an untrusted environment, which increases the amount of storage.

For example, the medical application 118 may use the secure element private key to encrypt one or more pairing secrets. The medical application 118 may cause the secure element 138 to encrypt the one or more pairing secrets using the secure element private key, for example. The one or more pairing secrets may be used by the medical application 118 to securely communicate with the medical device 104 and/or the server 110. In some implementations, the secure element 138 or the medical application 118 may store encrypted pairing secrets in the untrusted memory 122 of the personal device 102 or other untrusted memory, such as the cloud storage. The medical application 118 and/or the secure element 138 using the secure element private key may decrypt the encrypted pairing secrets and may delete the decrypted pairing secrets after use.

The personal device 102 may form an application authentication request that is sent to the server 110 to have the server 110 authenticate, authorize or verify the medical application 104 (508). The application authentication request may package, combine and/or include the secure element public key and one or more device identifiers, which the server 110 uses to authenticate the medical application 118. The one or more device identifiers may include an application secret, a phone number via a short message service (SMS) code, an e-mail address, a verification code entered into the application by a user, remote attestation of the operating system (OS) of the personal device 102 and/or proof of secure boot, remote attestation of the secure element 138, ownership of the medical device 104 via the medical device 104 being in proximity to the personal device 102 and verification of one or more embedded secrets of the medical device 104, a user pin code, or one more biometric identifiers of the user.

The one or more device identifiers may include an application secret, a verification code and/or one or more embedded secrets. The application secret may be embedded within the software code of the medical application 118. The one or more embedded secrets and/or the application secret may be provisioned during manufacturing. The verification code and/or the one or more embedded secrets of the medical device 104 may be provisioned at manufacturing, fabrication, packaging or distribution of the medical device 104, such as being written within a packaging or within a manual of the medical device 104. The one or more device identifiers may include the phone number and/or email address associated with the user of the personal device 102, which is compared to reference information for verification.

In some implementations, the medical application 118 may perform remote attestation with the phone, secure element or operating system maker to authenticate the operating system of the personal device 102 or secure element 138. The maker may verify a digital signature associated with the operating system, secure element or firmware to verify the integrity of the operating system, firmware, e.g., to ensure a secure boot, and/or the secure element 138. In some implementations, the server 110 verifies a pin code, user biometric, thumbprint or facial identification, or other user input to authenticate the medical application 118.

The personal device 102 may digitally sign the application authentication request prior to sending the application authentication request to the server 110 for authentication and/or digital certificate generation (510). The medical application 118 or secure element 138 may use the secure element private key to digitally sign the application authentication request so that the server 110 may verify the digital signature before the server 110 provides the digital certificate to the personal device 102.

Figure 8:
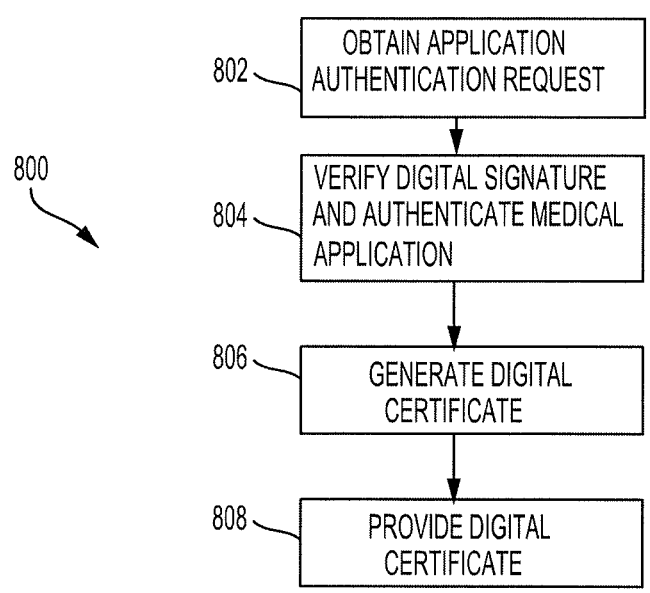
FIG. 8 is a flow diagram of an example process for generating the digital certificate using the secure communication system according to an aspect of the invention.

The personal device 102 may provide or send the application authentication request including the secure element public key and the one or more device identifiers to the server 110 to obtain a digital certificate (512). FIG. 8 describes the process by which the server 110 generates the digital certificate and provides the digital certificate to the personal device 102 in response to the application authentication request.

The personal device 102 using the medical application 118 may obtain the digital certificate from the server 110 via the network 108 or a denial (514). If the personal device 102 obtains a denial from the server 110, the personal device 102 may resend the application authentication request to the server 110. If the personal device 102 obtains the digital certificate, the medical application 118 of the personal device 102 may include the digital certificate in a pairing request and provide the pairing request to the medical device 104 to establish a secure connection (516).

The personal device 102 pairs with the medical device 104 and establishes the secure communication with the medical device 104 using one or more authentication factors including the certificate, a password, a hardware authentication token and/or a cloud authentication token, as described above in FIG. 3 (518). In some implementations, the medical application 118 may establish a shared secret between the personal device 102 and the medical device 104 to facilitate the secure communication. The shared secret may be based on the exchange of a device identity, the public key, the digital certificate, nonce value, or security proof between the personal device 102 and the medical device 104.

The medical application 118 of the personal device 102 may digitally sign the one or more payloads that are sensitive using the secure element private key after a secure communication has been established (520). The medical application 118 may identify the sensitivity, criticality, or importance of the payload based on a format of the data packets within the payload. The medical application 118 may digitally sign payloads, such as commands to administer or provide treatment or other messages, such as the acknowledgement command, that are critical or important to the functioning of the medical device 104 or are related to the security of the medical device 104. The medical application 118 may communicate the one or more sensitive payloads between the personal device 102 and the medical device 104. In some implementations, the digital signature may be computed using a secure hash output value and a monotonically increasing counter value.

The medical application 118 may send one or more payloads, such as a command control a function of the medical device 104, to the medical device 104 (522). For example, the command may control the administration of a treatment or medication, such as dispensing insulin. The one or more commands may require confirmation by a user via a PIN or user biometrics. In some implementations, the one or more commands may be authenticated using the primary private key.

Figure 6:
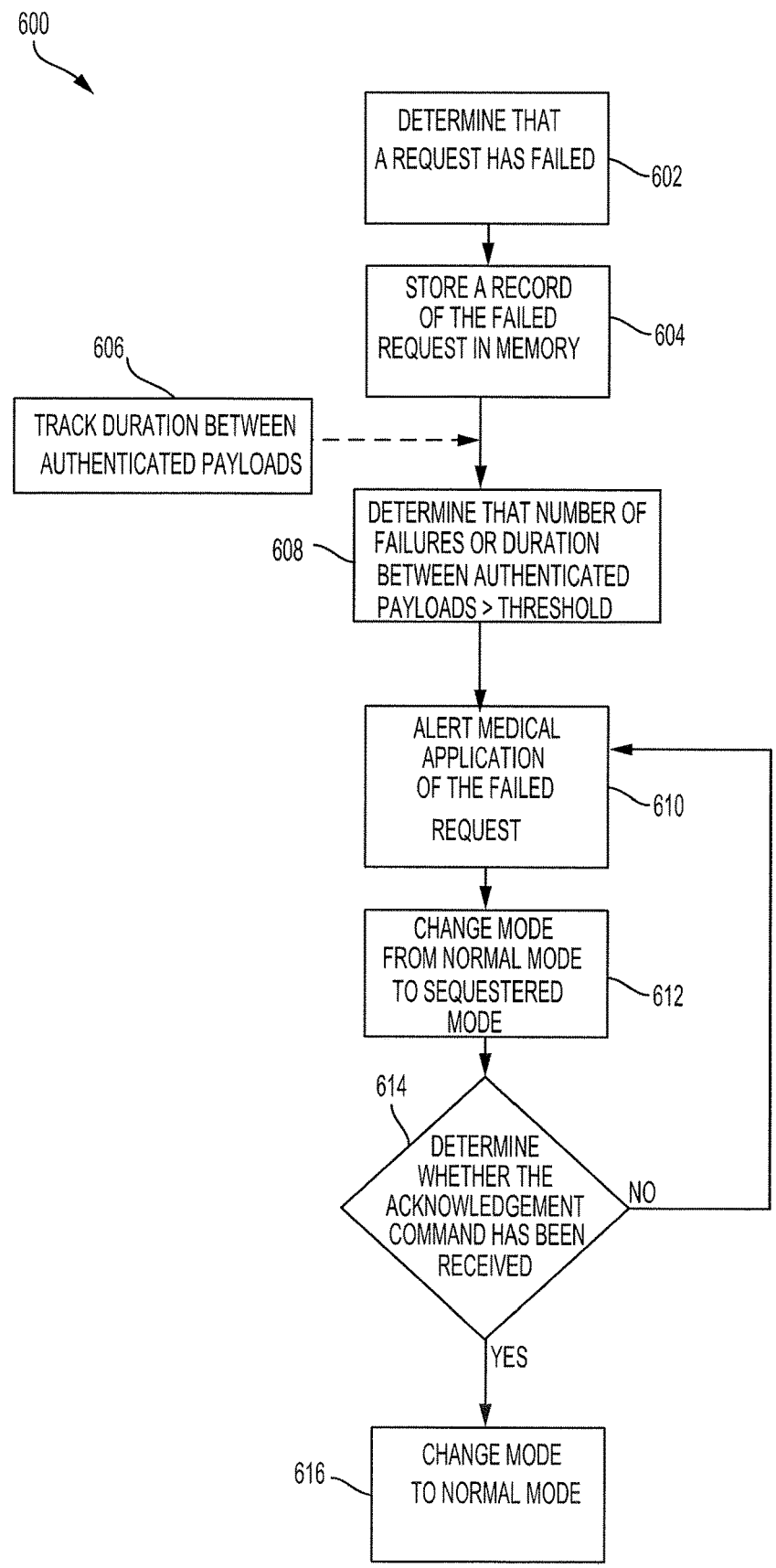
FIG. 6 is a flow diagram an example process of security measures of the secure communication system according to an aspect of the invention.

FIG. 6 is a flow diagram of a process 600 implemented on the medical device 104 to respond to a failed access or pairing request from the personal device 102 within the secure communication system 100. The one or more computers or data processing apparatuses, for example, the processor 132, appropriately programmed, may respond to a failed access or pairing request.

The medical device 104 may determine that a pairing request or an access request (or "request") has failed (602). The medical device 104 determines that a request has failed when the medical device 104 is unable to verify the signature associated with a certificate, message or other payload and/or when one or more authentication factors, immutable identities and/or device identifiers are unable to be authenticated. In some implementations, the medical device 104 may verify the format of the certificate, message or other payload and determine that the request has failed if the certificate, message or other payload is not correctly formatted.

The medical device 104 may determine that the request has failed when there is a signature or authentication failure. For example, when the medical device 104 is unable to verify a signature using a stored or extracted public key, the medical device 104 may determine that there has been a signature failure. In another example, when one or more authentication factors, one or more device identifiers, or one or more immutable identities are missing or do not match with corresponding reference information stored on the server 110 and/or the medical device 104, the medical device 104 may determine that there has been an authentication failure. In another example, when one or more authentication factors, such as a device certificate, have expired, the medical device may determine that there has been an authentication failure. If the medical device 104 determines that the request has failed the medical device 104 may store a record of the failed request in the memory 134 and/or the number of failed requests (604). The record of the failed request may include the type of request, such as a signature failure and/or authentication failure, and the nature of the failure, such as an incorrectly formatted message, a missing authentication factor, an incorrect or expired certificate, or an incorrect password. The record may include the time of the failure and/or the number of failures. For example, the medical device 104 may increment a counter value to track the number of each type of failure and a total number of failures.

The medical device 104 may use a timer and track the duration between authenticated payloads (606). The medical device 104 may determine that the number of failures exceeds a threshold amount within a particular duration or the duration between authenticated payloads exceeds a threshold time (608).

The medical device 104 may alert the medical application 118 of the failed request and/or lock out (610). The alert may cause the medical application 118 to alert the user that an acknowledgment command is required via the user interface. A lock out may prevent access to functions of the medical device 104, such as place the medical device 104 in a sequestered mode.

The medical device 104 may change its mode of operation from a normal mode to a sequestered mode after alerting the medical application (612). The sequestered mode may be an operating mode of the medical device 104 that ceases to administer treatment or medication to the patient. In some implementations, the sequestered mode may be an operating mode of the medical device 104 that ceases to recognize commands from the personal device 102. In some implementations, the sequestered mode may be an operating mode of the medical device 104 with enhanced security measures and allow only essential functions to operate. For example, limited commands, such as non-sensitive commands or messages, may be accepted but other commands, such as sensitive commands or messages, may be rejected. The normal made may be an operating mode of the medical device 104 that recognizes all commands from the personal device 102 and/or operates with minimal security measures.

The medical device 104 determines whether an indication, such as an acknowledgment command, has been received (614). The acknowledgement command may be a receipt acknowledgement indicating that the user has received the alert. In some implementations, the medical application 118 may return the acknowledgement command in response to verifying user input, such as biometric data or a PIN code.

The medical device 104 may obtain the indication, such as the acknowledgment command, and in response, the medical device 104 may change back to the normal mode (616). If the acknowledgment command is not received by the medical device 104, the medical device 104 may provide the alert to the medical application 118 again.

Figure 7:
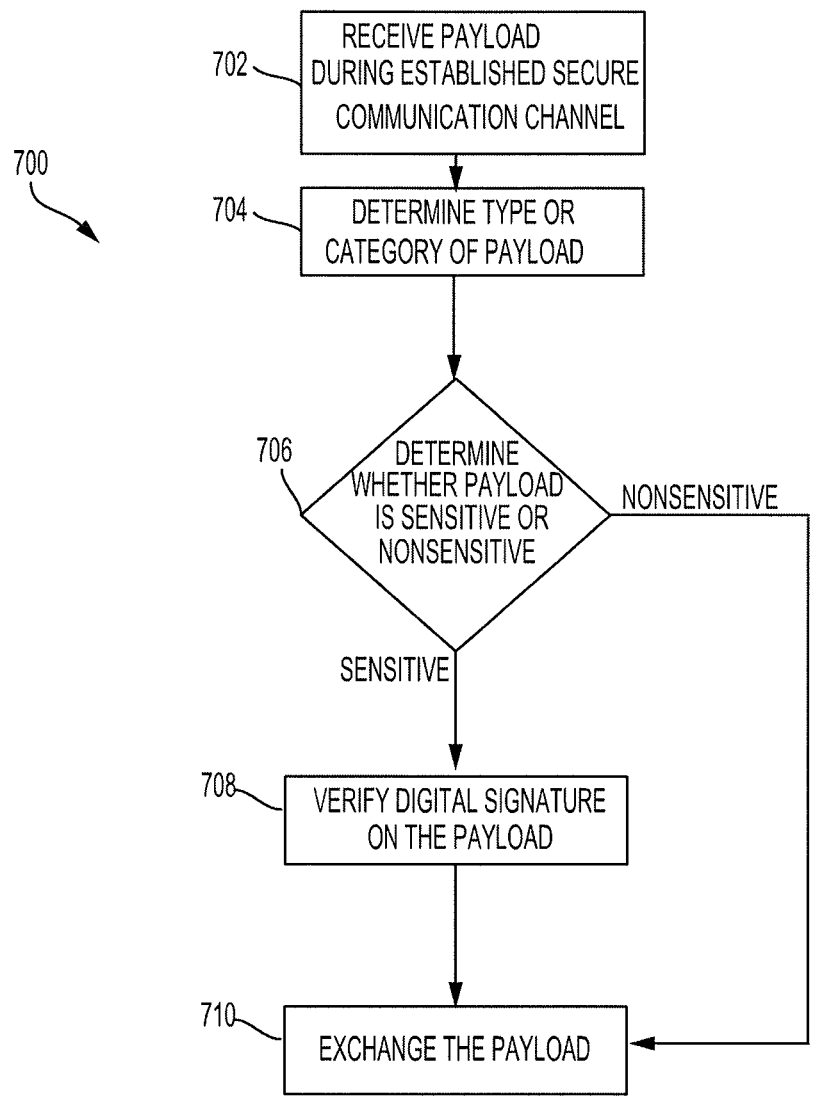
FIG. 7 is a flow diagram of an example process for exchanging sensitive and non-sensitive payloads using the secure communication system according to an aspect of the invention.

FIG. 7 is a flow diagram of a process 700 implemented on the medical device 104 to exchange sensitive and non-sensitive payloads with the personal device 102 within the secure communication system 100. The one or more computers or data processing apparatuses, for example, the processor 132, appropriately programmed, may exchange the sensitive and non-sensitive payloads.

Once secure communication has been established, the medical device 104 may exchange payloads with the medical application 118. The medical device 104 receives a payload during the established secure communication session (702). A payload may be a message, command or other data included within a data packet.

The medical device 104 determines the type or category of payload that was received (704). The medical device 104 may parse the payload and determine the type or category of the payload based on the format of the payload. For example, the payload may have a tag or other identifier, such as a set of bits in a particular location of the data packet that identifies the category or type of the payload. The medical device 104 compares the tag, format or other identifier to a mapping of different types or categories of payloads.

The medical device 104 determines whether the payload is sensitive or non-sensitive based on the type of payload (706). The medical device 104 may compare the type or category to a list or mapping of sensitive and non-sensitive data types to determine whether the payload is sensitive or non-sensitive. The sensitive payloads may include confidential data of the user and/or commands to operate the medical device 104. The different commands may include commands to control the administration of a treatment or commands to send and/or update information. For example, the command may control the administration of a treatment or medication, such as dispensing insulin. The non-sensitive payloads may include non-confidential data such as a current battery power level of the medical device 104.

If the medical device 104 determines that the payload is sensitive, the medical device 104 may verify the digital signature using a stored or included secure element public key (708). If the digital signature is verified, the medical device 104 may exchange the payload with the personal device 102 (710). If the digital signature is not verified, the medical device 104 may determine that the request has failed, as described above in FIG. 6, and does not exchange the payload. For example, the medical device may determine that the digital signature is invalid. In some implementations, the medical device 104 may determine that the sensitive payloads are digitally signed but the digital signature is no longer valid. If the medical device 104 determines that the payloads are non-sensitive, the medical device 104 may exchange the payload with the personal device 102 without the need for the digital signature (710).

FIG. 8 is a flow diagram of a process 800 implemented by the server 110 to generate and provide the digital certificate within the secure communication system 100. One or more computers or data processing apparatuses, appropriately programmed, may generate and provide the digital certificate to the personal device 102.

The server 110 obtains the application authentication request from the personal device 102 (802). The server 110 may parse or extract the one or more device identifiers and/or the secure element public key from the application authentication request.

The server 110 verifies the digital signature and authenticates the medical application 118 using the secure element public key and the one or more device identifiers (804). The server 110 may validate the digital signature on the application authentication request using the secure element public key and/or verify the one or more device identifiers. The server 110 may validate multiple device identifiers.

The server 110 may verify the presence of the application secret within the software code, e.g., provisioned during manufacturing or production, to authenticate the medical application 118. The server 110 may verify the presence of the embedded secret or determine that the verification code matches reference information to authenticate the medical application 118. The server 110 may compare the biometric information, personal identification number (PIN), or other user-specific information, such as phone number and/or email address, to stored reference information associated with the medical application 118 and authenticate the medical application 118 for the personal device 102 when the information matches. Similarly, the server 110 may ensure that the operating system, secure element 138 or secure boot has been remotely attested to and verified by the operating system or secure element maker.

If the server 110 authenticates the medical application 118, the server 110 may perform the functions of a certificate and/or a signature authority and generate a digital certificate from the secure element public key and the one or more device identifiers included in the application authentication request (806). The server 110 may sign the digital certificate using a server private key that may be verified by a corresponding server public key, which may be stored within the medical device 104. If the server 110 does not authenticate the medical application 118, the server 110 may issue a denial to the medical application 118. Once the digital certificate is generated, the server 110 provides the digital certificate to the personal device 102 (808).

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A device for providing secure communication, comprising:
   a secure element configured to generate application key pairs and perform cryptographic operations; and
   a trusted environment that is physically or logically isolated from an untrusted environment and having:
   a memory configured to store an application, and
   one or more processors configured to perform operations of the application that execute within the trusted environment, the operations comprising:
      generating, using the secure element, an application key pair that includes a secure element private key and a secure element public key to obtain a digital certificate,
      sending an application authentication request including one or more device identifiers and the secure element public key to a server,
      obtaining, from the server, the digital certificate,
      providing the digital certificate to a second device,
      digitally signing, using the secure element private key, one or more sensitive payloads that include a command to administer or provide treatment to a patient, and
      providing the one or more digitally signed sensitive payloads that include the command to administer or provide treatment to the patient to the second device.

2. The device of claim 1, wherein the operations further comprise:
   digitally signing the application authentication request prior to sending the application authentication request to the server;
   wherein the digital certificate that is obtained from the server was digitally signed by the server.

3. The device of claim 1, wherein the one or more device identifiers include at least one of an application secret, a phone number via a short message service (SMS) code, an e-mail address, a verification code entered into the application by a user, remote attestation of the device, remote attestation of the secure element, ownership of an embedded device via one or more embedded secrets of the embedded device, a user pin code, or one or more biometric identifiers of the user.

4. The device of claim 3, wherein the operations further comprise:
   using the secure element private key to both encrypt and decrypt at least one of application data or secrets for storage in an untrusted environment.

5. The device of claim 1, wherein the operations further comprise:
   determining a sensitivity of one or more payloads based on a format of data packets within the one or more payloads; and
   determining that that the one or more payloads are sensitive based on the sensitivity.

6. The device of claim 5, wherein the digital signature is computed using a secure hash output value and a monotonically increasing counter value.

7. The device of claim 1, wherein the operations further comprise:
   establishing, by the application, a shared secret between the device and the second device, the shared secret being based on an exchange of at least one of a device identity, a public key, the digital certificate, a nonce value, or a security proof between the device and the second device.

8. A system for providing secure communication, comprising:
   a medical device configured to provide or administer a medical treatment to a patient;
   a server configured to generate a digital certificate that includes a secure element public key and one or more device identifiers in response to authenticating a medical application; and
   a personal device including:
      a secure element configured to generate an application key pair that includes a secure element private key and the secure element public key and perform cryptographic operations,
      a memory configured to store the medical application, and
      one or more processors configured to perform operations of at least one of the medical application or the secure element that execute within a trusted environment, the operations comprising:
         generating the application key pair that includes the secure element private key and the secure element public key using the secure element to obtain the digital certificate,
         providing an application authentication request that includes the one or more device identifiers and the secure element public key to the server,
         obtaining, from the server, the digital certificate that includes the secure element public key and the one or more device identifiers,
         providing the digital certificate to the medical device, and
         establishing a secure communication channel between the personal device and the medical device using the digital certificate;
      wherein the medical device is further configured to verify the digital certificate that is provided from the medical application using a server public key, the secure element public key and the one or more device identifiers.

9. The system of claim 8, wherein the server is further configured to:
   obtain the application authentication request including the one or more device identifiers;
   authenticate the medical application using the one or more device identifiers including matching the one or more device identifiers to reference information that indicates the medical application was downloaded on the personal device; and
   provide the digital certificate to the medical application in response to authenticating the medical application.

10. The system of claim 9, wherein the one or more device identifiers includes identifying information of a user, identifying information of the personal device, or identifying information of the medical application.

11. The system of claim 8, wherein the operations further comprise:
   digitally signing, using the secure element private key, one or more sensitive payloads that include a command to administer or provide the medical treatment to the patient; and
   exchanging, between the personal device and the medical device, the one or more sensitive payloads.

12. The system of claim 8, wherein the medical device comprises:

a memory configured to store a record of at least one of an authentication failure or a signature failure of a message between the medical device and the personal device and a counter of a number of records of the at least one of the authentication failure or the signature failure for messages.

13. The system of claim 12, wherein the medical device further comprises:
one or more processors configured to:
alert the medical application that an alert acknowledgement command is required in response to the at least one of the authentication failure or the signature failure; and
switch to a sequestered operation mode that has more security measures and allows only limited commands from a normal mode of operation that recognizes all commands from the personal device.

14. The system of claim 13, wherein the one or more processors of the medical device are further configured to:
cause the medical application to notify a user that the alert acknowledgement command is required;
determine that the alert acknowledgement command has been received; and
switch to the normal mode of operation from the sequestered operation mode.

15. The system of claim 8, wherein the medical device includes:
a memory configured to store the server public key, wherein the server public key is provisioned during manufacturing, distribution or production; and
one or more processors configured to:
obtain, from the medical application, the digital certificate,
store the secure element public key in the memory, and
establish communication with the medical application.

16. A method for securely communicating between a medical device and an application on a personal device in a secure computing environment, comprising:
generating, by the application and using a secure element, a key pair including a secure element private key and a secure element public key to obtain a digital certificate, the application being stored within a trusted environment of the personal device;
storing, by the application and within the secure element, the secure element private key;
sending, by the application and to a server, an application authentication request including the secure element public key and one or more device identifiers;
verifying, by the server, the application authentication request;
generating, by the server, the digital certificate;
obtaining, by the application, the digital certificate from the server;
digitally signing, by the application and using the secure element public key, one or more sensitive payloads that include a command to administer or provide treatment to a patient; and
providing, by the application, the one or more digitally signed sensitive payloads that include the command to administer or provide treatment to the patient to the medical device.

17. The method of claim 16, wherein generating, by the application and using the secure element, the key pair including the secure element private key and the secure element public key includes:
generating, using the secure element, a primary key pair comprising a primary private key and a primary public key and generating, in the secure element, a secondary key pair comprising a secondary private key and a secondary public key, wherein user identity authentication is required to use the primary private key.

18. The method of claim 17, further comprising:
sending, by the application, one or more commands to the medical device, wherein the one or more commands require confirmation by a user via at least one of a pin or user biometrics, wherein the one or more commands are authenticated using the primary private key.

19. The method of claim 16, further comprising:
encrypting, by the application using the secure element private key, one or more pairing secrets used by the application for communicating with the medical device and the server;
storing, by the application, the encrypted pairing secrets outside of the secure element;
decrypting, by the application, the encrypted pairing secrets using the secure element private key; and
deleting, by the application, the decrypted pairing secrets after the application has used the decrypted pairing secrets.

20. A method for secure communication, comprising:
generating, by an application that is stored within a trusted environment of a personal device and using a secure element, a key pair including a secure element private key and a secure element public key;
storing, by the application and within the secure element, the secure element private key;
encrypting, by the application using the secure element private key, one or more pairing secrets used by the application for communicating with a medical device or a server;
storing, by the application, the one or more encrypted pairing secrets in an untrusted environment;
decrypting, by the application, the encrypted pairing secrets using the secure element private key; and
deleting, by the application, the decrypted pairing secrets after the application has used the decrypted pairing secrets.

21. The method of claim 20, further comprising:
sending, by the application and to the server, an application authentication request including the secure element public key and one or more device identifiers;
verifying, by the server, the application authentication request;
generating, by the server, a digital certificate;
obtaining, by the application, the digital certificate from the server; and
establishing, by the application, a secure communication channel between the personal device and the medical device using the digital certificate.

* * * * *